United States Patent [19]

Hidy et al.

[11] 3,965,275

[45] June 22, 1976

[54] COMPOSITION AND METHOD

[75] Inventors: Phil H. Hidy, Terre Haute; Robert S. Baldwin, Montezuma, both of Ind.

[73] Assignee: Commercial Solvents Corporation, Terre Haute, Ind.

[22] Filed: May 12, 1975

[21] Appl. No.: 576,639

Related U.S. Application Data

[63] Continuation of Ser. No. 441,150, Feb. 11, 1974, abandoned, which is a continuation of Ser. No. 289,456, Sept. 15, 1972, abandoned, which is a continuation of Ser. No. 28,913, April 15, 1970, abandoned, which is a continuation-in-part of Ser. No. 512,199, Dec. 7, 1965, abandoned.

[52] U.S. Cl. ............................................. 424/279
[51] Int. Cl.² ...................................... A61K 31/365
[58] Field of Search .................................. 424/279

[56] References Cited
UNITED STATES PATENTS

| | | | |
|---|---|---|---|
| 3,239,341 | 3/1966 | Hodge et al. ...................... | 424/279 |
| 3,239,342 | 3/1966 | Hodge et al. ...................... | 424/279 |
| 3,239,345 | 3/1966 | Hodge et al. ...................... | 424/279 |
| 3,239,347 | 3/1966 | Hodge et al. ...................... | 424/279 |

OTHER PUBLICATIONS

Goodman et al., The Pharmaceutical Basis of Therapeutics, 3rd Ed., pp. 1382, 1383, 1541–1544, 1548–1552, The MacMillan Co. N.Y. (1965).

Chemical Abstracts vol. 72: 53749u; vol. 72: 41764g; vol. 69: 1932s; vol. 69: items 1933t, 42911c, 42912d, 86648b, 86649c, 86650w, 86651x, 86652y, 86653z, 86654a, 86655b, 96505s and 106281g.

*Primary Examiner*—Donald B. Moyer
*Attorney, Agent, or Firm*—Morton, Bernard, Brown, Roberts & Sutherland

[57] ABSTRACT

A process, and the composition used therein, for estrogenic therapy which comprises administering daily to the patient from about 0.2 to 2000 milligrams of a compound having the formula:

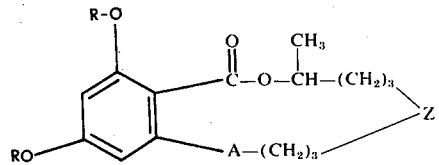

wherein R is selected from the group consisting of hydrogen, lower alkyl and a lower saturated acyclic acyl; Z is selected from the group consisting of $>CH_2$, $>CHOH$ and $>C=O$; and A is selected from the group consisting of $-CH_2-CH_2-$ and $-CH=CH-$.

6 Claims, No Drawings

COMPOSITION AND METHOD

This is a continuation of application Ser. No. 441,150, filed Feb. 11, 1974; which in turn is a continuation of application Ser. No. 289,456, filed Sept. 15, 1972; which in turn is a continuation of application Ser. No. 28,913, filed Apr. 15, 1970; which in turn is a continuation-in-part of application Ser. No. 512,199, filed Dec. 7, 1965 all of which are abandoned.

The present invention is directed to a pharmaceutical composition useful in carrying out estrogenic therapy for human patients.

The administration of estrogenic hormones such as estradiol and estrogenic substances such as diethylstilbestrol in the therapeutic treatment of various illnesses and disorders such as acne, capillary fragility, emotional instability, delayed puberty, reduction of blood cholesterol and habitual abortion, has been practiced for years with considerable success. The estrogen hormones and estrogenic substances currently available are not without criticism, however. A major drawback of these substances, particularly as applied to their administration in men, is their strong "feminizing" effect. Many women also manifest undesirable side-effects from these compounds, as, for example, excessive menstrual flow and masculinization. A search has been in progress for years with little success for a "weak estrogen" compound which is effective in estrogenic therapy but lacks distinct feminizing and other undesirable side effects.

In accordance with the present invention, there is provided a pharmaceutical composition containing an effective therapeutically active estrogenic ingredient characterized by relatively weak feminizing and other side effect estrogenic activity.

The active ingredient of the pharmaceutical compositions can be represented by the structural formula:

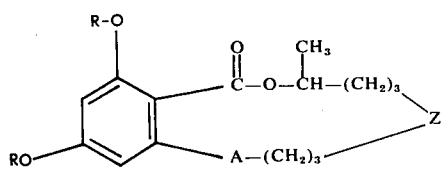

wherein R is hydrogen, substituted or unsubstituted alkyl, e.g. lower alkyl such as methyl, ethyl, hexyl, etc., and acyl, e.g., lower saturated acyclic acyl radicals such as acetyl and valeryl; A is $-CH_2-CH_2-$ or $-CH=CH-$ and Z is $>C=O$, $>CH_2$ or $>CHOH$. As will be demonstrated below, the compounds of the invention when compared with diethylstilbestrol, a compound of known estrogenic activity used in estrogenic therapy in the mouse uterotropic activity test, exhibit effective but relatively weak estrogenic activity.

The compounds of the present invention include the compound:

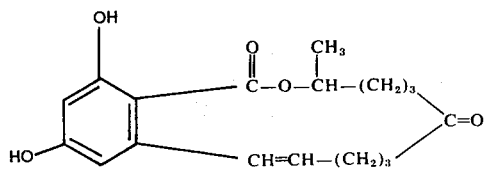

hereinafter referred to as the fermentation estrogenic substance (F.E.S.), from which the other compounds of the invention can be produced by reduction of the ketone group to replace the oxygen of the ketone group with two hydrogen atoms, by reducing the ketonic group to add two hydrogens thereto, by saturation of the olefinic bond or any combination of such reductions. The reduction of the ketone group to replace the oxygen can be effected by several procedures. One of these procedures involves the Clemmensen reduction using zinc and hydrochloric acid; another involves the Wolff-Kishner reduction using hydrazine and alkali, e.g. NaOH, and the third involves formation of the dithioacetal with ethylene dithiol or ethylmercaptan and the catalytic desulfurization with Raney nickel catalyst containing adsorbed hydrogen.

The addition of two hydrogen atoms to the ketonic group and saturation of the olefinic bond can be obtained by conventional reduction procedures, for instance, in the presence of Raney nickel catalyst. The reduction is preferably carried out with the F.E.S. suspended or dissolved in a suitable solvent, e.g. an alcohol, preferably a lower alkanol such as methanol, ethanol, etc. In general, the reduction can be accomplished at ambient temperatures and ambient pressures. Preferable temperatures are from about 15° to 40°C., and preferable pressures are of from about 1 to 100 atmospheres. In general, from about 0.1 to 5 grams of catalyst are used per gram of F.E.S.

In producing compounds of the invention where A is $-CH_2-CH_2-$ the olefinic bond of F.E.S. can be reduced, for example, by hydrogenation in the presence of a Group VIII metal, particularly platinum or palladium catalyst on a suitable carrier, e.g., charcoal. Generally, the catalyst contains from about 0.01 to about 10% of the catalytic metal. The catalyst is used in a ratio of generally from 0.02 to 2 grams of catalyst, preferably about 0.1 to 0.5 gram, and particularly about 0.2 gram catalyst per gram of F.E.S. The reduction may be carried out while the F.E.S. is dissolved in a suitable solvent, e.g. an alcohol, especially a lower alkanol such as 2-propanol, methanol, ethanol, and acid, e.g. acetic acid, etc. at ambient temperatures; e.g. from about 15° to 40° C., and ambient pressures, since only the presence of hydrogen is required; however, it is preferred to utilize an elevated pressure, e.g. from about 1 to 50 atmospheres of hydrogen.

In producing compounds of the present invention where R is alkyl, conventional alkylation procedures can be used to replace the H atom of one or both of the OH groups on the benzene ring of F.E.S. with an alkyl group. Alkylated dihydro F.E.S. compounds can be produced, for example, by first alkylating F.E.S. and then reducing it as set forth supra, or by first reducing it and then alkylating it. The alkylation can be by reaction with the corresponding dialkyl sulfates, e.g. dimethyl sulfate, diethyl sulfate, etc., to produce the dialkyl F.E.S. or a monoalkyl F.E.S. with the alkyl group replacing the hydrogen of the hydroxyl group on the benzene ring ortho to the ester group. Furthermore, a monomethyl F.E.S. compound with the methyl group replacing the hydrogen of the hydroxyl group para to the ester group can be selectively produced using diazomethane.

In producing compounds of the present invention where R is acyl, conventional acylation procedures can be used to replace the hydrogen atom of one or both of the hydroxyl radicals on the benzene ring of F.E.S. with an acyl radical. Acylated F.E.S. compounds can be produced, for example, by reaction with the corresponding acid anhydride, e.g. acetic anhydride, propionic anhydride, etc., catalyzed with, for example, sodium acetate or pyridine. Ambient conditions can be used although it is preferred to keep the reaction mixture cold. When compounds having one R as alkyl and the other acyl, it is advantageous to alkylate before acylating.

The fermentation estrogenic substance (F.E.S.) is so named since a convenient method for producing it is by cultivating, on a suitable nutrient medium, the organism *Gibberella zeae* (Gordon) on deposit at the Northern Utilization Research and Development Division of the United States Department of Agriculture under the number NRRL-2830.

Specific examples of the preparation of F.E.S. and other compounds of the invention are given below and disclosed in more detail in U.S. Pat. Nos. 3,196,019; 3,239,354; 3,239,345 and 3,239,341.

The pharmaceutical compositions of the invention can be prepared by mixing the active ingredient with non-toxic, pharmaceutically-acceptable carriers, which can be inert diluents or solid carriers, and forming the resulting mixture into suitable dosage unit forms. The compositions can be administered to the subject by any suitable method including oral and parenteral administration. Forms suitable for oral administration include, for example, pressed or coated tablets, capsules or pills, syrups, solutions or suspensions in water or non-toxic organic solvent media such as propylene glycol and glycerol formal, and dispersible powders. Compositions suitable for parenteral administration are the known pharmaceutical forms for such administrations, for example, sterile aqueous suspensions or solutions in oily media. The sterile aqueous suspensions can be formulated in the presence of parenterally acceptable buffers, e.g. sodium citrate, citric acid and/or preservatives such as phenol and methyl and propyl esters of p-hydroxy benzoic acid. A preferred oily media for preparation of the sterile aqueous solution is peanut oil. For treatment of the skin, the active ingredient can be mixed in any of the conventional cosmetic base lotions in a hydrophilic base.

The pharmaceutical compositions may also include adjuvants known in the art as desirable or useful as, for example, wetting agents, dispersing agents, suspending agents, lubricating agents, sweetening agents, coloring agents and flavoring agents.

Illustrative of oral compositions are tablets wherein the active ingredient is mixed with inert fillers, e.g., dicalcium phosphate, terra alba or lactose in the presence of disintegrating agents as, for example, maize starch and in the presence of lubricating agents such as magnesium stearate. Examples of suitable aqueous solutions for oral use are those formulated by incorporating the active ingredient in inert pharmaceutically-acceptable liquid solvent media which can contain, if desired, pharmaceutically-acceptabe thickening agents such as sodium carboxy-methyl-cellulose and/or pharmaceutically-acceptable sweetening and flavoring agents.

The actual amounts of the active ingredient in the pharmaceutical composition of the invention may vary depending on the particular disorder treated but in all cases the amount present is that sufficient to produce the desired therapeutic effect. In general, for carrying out estrogenic therapy for a human patient from about 0.2 to 2000 milligrams of the active ingredient are administered daily. This amount is administered in amounts of from about 0.2 to 500 mg. preferably 1.0 to 100 mg. per dosage unit. More particularly, in postmenopause usage the active ingredient will be administered in a range of about 0.1 to 10 mg., preferably about 0.5 or 1 to 6 mg. per day per kilogram body weight of the patient. With females this dosage is typically administered in a manner similar to oral contraceptives, that is, 20 to 25 days on the drug followed by rest periods of up to ten days, e.g. 5 to 10 days. Often this cycle is referred to as 3 weeks on the drug and 1 week rest period. Post-menopause usage and the dosages used therefore includes treatment of capillary fragility and emotional instability and such dosages are those used with habitual abortion, delayed puberty, etc. The cycle regime is used to to avoid building of endometrium as is well known. The dosage for treatment of cholesterol, i.e. for cholesterol lowering, is from about 0.5 to 20 mg./day/kilogram of body weight and the dosage is usually given continuously although cyclic administration can be used. Acne is treated with a skin cream containing the active ingredient, e.g. 0.1 to 10 wt. % of the active ingredient in a cosmetic base lotion or in a hydrophilic base.

The following examples are offered to illustrate this invention; however, the invention is not limited to the specific materials, amounts and procedures set forth. The first example illustrates preparation of a suitable inoculum containing the organism *Gibberella zeae* (Gordon) NRRL-2830.

EXAMPLE I

A spore sand culture containing *Gibberella zeae* (Gordon) NRRL-2830 was aseptically placed in a sterile tube containing 15 milliliters of Czapek's-Dox solution and a small amount of agar. This medium was then incubated for about 168 hours at approximately 25°C. At the end of the incubation period, the medium was washed with 5 milliliters of sterile deionized water and transferred to a sterile tube containing 45 milliliters of Czapek's-Dox solution. The contents of the tube were then incubated for about 96 hours at about 25°C. after which the material was available for use in inoculation of a fermentation medium.

The following example illustrates the fermentation of the organism *Gibberella zeae* (Gordon) NRRL-2830 to produce F.E.S.

EXAMPLE II

To a 2 liter flask was added 300 grams of finely divided corn. The flask and its contents were then sterilized and after sterilization 150 milliliters of sterile deionized water were added. To the mixture in the flask were then added 45 milliliters of the inoculum prepared by the process of Example I and the material was thoroughly mixed. The mixed material was then incubated for about 20 days at 25°C. in a dark room in a water-saturated atmosphere.

The following example illustrates the recovery of the F.E.S. from the fermentation medium.

EXAMPLE III

A 300 gram portion of fermented material produced by the method of Example II was placed in 500 milliliters of deionized water and slurried. The slurry was then heated for about 15 minutes at 75°C., 300 grams of filter aid were then added and the material was filtered. The solid filtered material containing the F.E.S. was then air dried, and 333 grams of the dried cake were then extracted with 500 milliliters of ethanol. This procedure was repeated three more times. The ethanol extract was evaporated to dryness under vacuum to give 6.84 grams of solid material. This solid material was then dissolved in 20 milliliters of chloroform and extracted with 30 milliliters of an aqueous solution containing 5% by weight of sodium carbonate having an adjusted pH of about 11.2. The extraction process was repeated seven more times. The pH of the sodium-carbonate extract was then adjusted to 6.2 with hydrochloric acid, to yield a F.E.S. substance-containing precipitate. The precipitate and the aqueous sodium-carbonate extract were then each in turn extracted with 75 milliliters of ethyl ether. This procedure was repeated three more times to yield a light yellow ethereal solution, which was then evaporated to yield 116 milligrams of solid F.E.S. This material was then subjected to multiple transfer countercurrent distribution using 100 tubes and a solvent system consisting of two parts chloroform and two parts carbon tetrachloride as the lower phase and four parts methanol and one part water as the upper phase, all parts by volume. The solid material obtained from the multiple transfer countercurrent distribution was F.E.S.

The following examples, Examples IV to VI, illustrate the reduction of F.E.S. to produce tetrahydro F.E.S. having the formula:

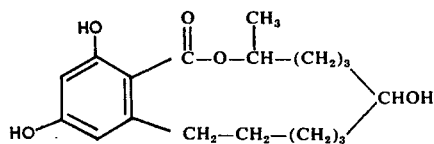

EXAMPLE IV

Tetrahydro F.E.S. was produced by dissolving 0.5 gram F.E.S. in 200 milliliters of ethanol. The F.E.S. was reduced by contacting the solution with hydrogen for 3 hours at 30°C. with 1000 psi using 2 grams of Raney nickel as a catalyst. After filtering and concentrating the reaction mixture, the product was washed with 2 to 3 milliliters of 2-nitropropane and crystallized. It was found to have a melting point from 143°–160°C.

EXAMPLE V

The reduction of F.E.S. was conducted in methanol at 30°C. and 1000 psi hydrogen pressure for 5 hours using Raney nickel catalyst to provide a product melting, after several crystallizations from 2-nitropropane and nitromethane, at 141°–143°C. and analyzing:

| Calc. | ($C_{18}H_{26}O_5$) | Found |
|---|---|---|
| % C | 67.1 | 67.2 |
| % H | 8.14 | 8.28 |

EXAMPLE VI

The reduction of 1 gram of F.E.S. was conducted in 150 cc. of ethanol at room temperature and 50 psi of hydrogen for 4 hours in the presence of a small amount of Raney nickel (about 1 cc. of a thick suspension in water). The product was concentrated, treated with 5 milliliters of isopropyl alcohol, cooled and filtered. The filtrate was mixed with 5 milliliters of water, left standing over night, cooled and filtered to provide 0.65 gram of product having a melting point of 147°–157°C. This product was recrystallized from isopropyl alcohol-water mixtures two times to provide 0.18 gram of a product having a melting point of 178°–180°C. A product having a melting point of 146°–148°C. and weighing 0.22 gram was also recovered from the filtrate after the first recrystallization of the product weighing 0.65 gram. The reduction of the ketone group introduces an asymmetric carbon atom and makes diastereoisomers possible. The optical activities of the two products were (1) for THFES(HM), the product with a melting point of 178°–180°C., $[\alpha]_D^{25}$ = about + 46° e.g. and (2) for a combination of the THFES(HM) and THFES(LM), the combination product having a melting point of 146°–148°C., $[\alpha]_D^{25}$ = about +39° e.g. where $[\alpha] = \alpha.100/c.1$, $c = 1\%$ in methanol and $l=2$ dm. This product is actually a mixture (about 1:2) of the product melting at 178°–180°C. and its isomer. The low melting isomer can be obtained in pure form by recrystallization out of the combination product using glacial acetic acid to provide pure THFES(LM) which melts at ~155°C. and has optical activity $[\alpha]_D^{25}$ =+36°.

The following example illustrates the preparation of deoxy tetrahydro F.E.S.

EXAMPLE VII

Two 10 gram portions of F.E.S., each in 200 milliliters acetic acid, were catalytically reduced at room temperature in the presence of 1.2 grams of PdO catalyst at a hydrogen pressure of about 45 psi. The combined reduction mixtures were heated to boiling, filtered, and the filter cake was washed with 50 milliliters of hot acetic acid. The cooled filtrate was added, with stirring, to 2 liters of water. The mixture was stirred for 15 minutes and the white solid was collected by filtration, washed and dried in a vacuum desiccator to yield 19.1 grams of dihydro F.E.S. in which the ethylenic unsaturation is saturated, and having a melting point of 191°–193°C.

The dihydro F.E.S. (1 gram) is added slowly with cooling (ice-bath), to a mixture of 5 cc. of ethylene dithiol 0.25 gram of freshly fused zinc chloride and 2 grams of anhydrous sodium sulfate, contained in a microflask. The mixture is maintained at 5°C. for 20 hours and then at room temperature for 4 hours, whereupon it is poured into 50cc. of ice and the precipitate is collected and subjected to hydrogenolysis. To the reaction product is added 100 cc of 90% ethanol and 15 grams of Raney nickel catalyst and the mixture is refluxed until the reaction is complete. The nickel is removed by centrifugation and is washed several times with hot ethanol by centrifugation followed by decantation, and the centrifugates are combined. The mixture is evaporated to dryness and the residue is suitably recrystallized to yield deoxy THFES having the formula:

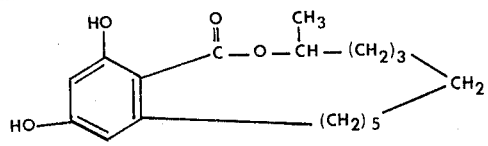

EXAMPLE VIII

Nitrosomethylurea in an amount of 1.2 grams was slowly added to a cold mixture of 3.6 milliliters of 50% potassium hydroxide and 17 milliliters of ether. After a few minutes the yellow ether layer of the mixture was decanted, dried over potassium hydroxide, and then added to a solution of 0.30 grams F.E.S. in 17 milliliters of ether. The resulting yellow mixture was left overnight in a loosely stoppered flask and then ether and diazomethane were evaporated using a steam bath. The remaining gummy residue was crystallized by adding 3 milliliters of water, heating to 60°C., and adding ethanol almost to solution. On cooling, crystals formed yielding 0.137 gram of a product having a melting point of 111°–122°C. and analyzing:

| Calc. | ($C_{19}H_{24}O_5$) | Found |
|---|---|---|
| % C | 68.7 | 68.3 |
| % H | 7.28 | 7.38 |
| % $OCH_3$ | 9.34 | 9.17 |

The p methyl F.E.S. is substituted for the F.E.S. in following essentially the same procedure used in Example VII to produce a compound having the formula:

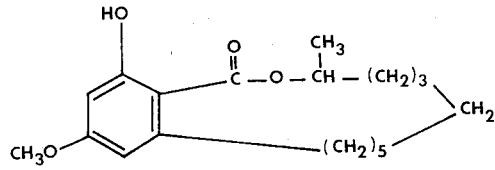

The following example illustrates the production of dimethyl F.E.S. and monomethyl F.E.S. derivatives, the monomethyl F.E.S. derivative having the hydrogen in the hydroxyl group ortho to the ester group replaced with a methyl group.

EXAMPLE IX

Dimethyl sulfate (5 milliliters) was added to a solution of 2.24 grams of F.E.S. in 80 milliliters 10% NaOH and 20 milliliters water. The mixture was stirred for one-half hour at 18°–20°C. (cooling bath) and an additional 5 milliliters of dimethyl sulfate was added. After an additional 70 minutes of stirring at 20°–26°C., the solid precipitate, Solid A, was collected by filtration, washed with water and dried in a vacuum desiccator. The filtrate from Solid A was acidified with 25 milliliters 12 N $H_2SO_4$ to yield a second precipitate, Solid B, which was collected, washed with water, and dried.

Solid A (0.79 gram having a melting point of 114°–118°C.) was recrystallized from a mixture of 10 milliliters water and 15 milliliters ethanol to yield 0.66 gram of dimethyl F.E.S. having a melting point of 108°–110°C.

Solid B (1.39 grams having a melting point of 152°–162°C.) was recrystallized twice from a mixture of water and alcohol to yield 0.8 gram of monomethyl F.E.S. having a melting point of 169°–174°C. and the following analysis of recrystallized Solid B (monomethyl F.E.S.) was obtained:

| Calc. | ($C_{19}H_{24}O_5$) | Found |
|---|---|---|
| % C | 68.65 | 67.97 |
| % H | 7.28 | 7.16 |
| % OMe | 9.34 | 9.28 |

Each of the o methyl F.E.S. and the dimethyl F.E.S. is substituted for the F.E.S. in the procedure of Example VII to produce the respective compounds:

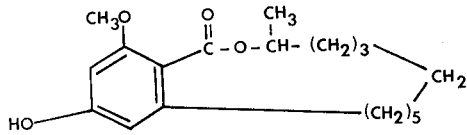

and

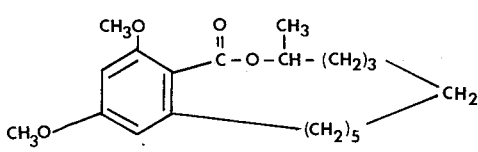

The following example illustrates the production of an acylated monomethyl F.E.S. derivative.

EXAMPLE X

To a solution of 368 milligrams of p methyl F.E.S. in 8 milliliters pyridine is added 5 milliliters acetic anhydride and the mixture is held at room temperature for 16 hours. Twenty-five milliliters of water are then added. The mixture is stored in a refrigerator for 2 hours. The solid precipitated is collected by filtration, washed with water and dried in a vacuum desiccator to recover a compound which is substituted for the F.E.S. in the procedure of Example VII to produce a compound of the formula:

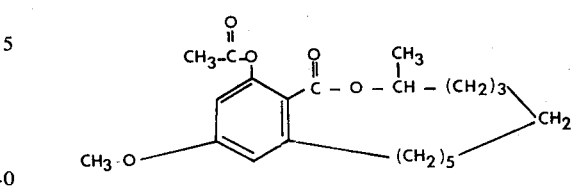

which is recovered.

EXAMPLE XI

The compound:

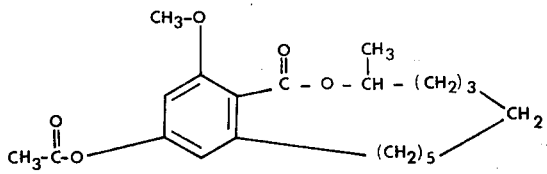

is produced by substituting o methyl F.E.S. for the dihydro F.E.S. in the procedure of Example VII.

The following example illustrates the reduction of F.E.S. to produce dihydro F.E.S. having the structure:

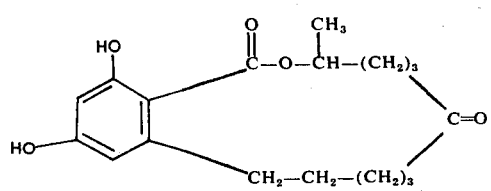

EXAMPLE XII

Two 10-gram portions of F.E.S. each in 200 milliliters acetic acid were catalytically reduced at room temperature in the presence of 1.2 grams of PdO catalyst at a hydrogen pressure of about 45 psi. The combined reduction mixtures were heated to boiling, filtered, and the filter cake was washed with 50 milliliters of hot acetic acid. The cooled filtrate was added, with stirring, to 2 liters of water. The mixture was stirred for 15 minutes and the white solid was collected by filtration, washed and dried in a vacuum desiccator to yield 19.1 grams of dihydro F.E.S. having a melting point of 191°–193°C.

The production of dimethyl dihydro F.E.S. is illustrated by the following Example.

EXAMPLE XIII

Dihydro F.E.S. (556 milligrams) was dissolved in 25 milliliters 10% NaOH and 10 milliliters water and the solution was stirred. To the stirred solution was added three, two-milliliter portions of dimethyl sulfate at half-hour intervals followed by stirring for an additional hour. The mixture was acidic and it was made alkaline by the addition of 10 milliliters 10% NaOH and the alkaline mixture was stirred one-half hour. The solid formed was collected by filtration, washed with water and dried in a vacuum desiccator. The product weighed 526 milligrams and melted at 115°–117°C. Recrystallization from a mixture of 10 milliliters of water and 25 milliliters of ethanol provided 371 milligrams of material having a melting point of 124°–125.5°C. It was analyzed with the following results:

| Calc. | $(C_{20}H_{28}O_5)$ | Found |
| --- | --- | --- |
| % C | 68.95 | 69.02 |
| % H | 8.10 | 8.12 |
| % $CH_3O$ | 17.81 | 17.81 |

The following example illustrates the production of monomethyl and dimethyl dihydro F.E.S., the monomethyl dihydro F.E.S. having a methyl group which replaced the hydrogen of the hydroxyl group on the benzene ring ortho to the ester group.

EXAMPLE XIV

Dimethyl sulfate (5 ml.) was added to a solution of 2.24 g. F.E.S. in 80 ml. of a 10% NaOH solution and 20 ml. of water. The mixture was stirred for one-half hour at 18°–20°C. (cooling bath) and an additional 5 ml. of dimethyl sulfate was added. After an additional 70 minutes of stirring at 20°–26°C., the solid precipitate, Solid A, was collected by filtration, washed with water and dried. The filtrate from Solid A was acidified with 25 ml. 12N $H_2SO_4$ to yield a second precipitate, Solid B, which was collected, washed with water, and dried.

Solid A (0.79 g. having a melting point of 114°–118°C.) was recrystallized from a mixture of 10 ml. water and 15 ml. ethanol to yield 0.66 g. of dimethyl F.E.S. having a melting point of 108°–110°C.

Solid B (1.39 g. having a melting point of 152°–162°C.) was recrystallized twice from a mixture of water and alcohol to yield 0.80 g. of monomethyl F.E.S. product having a melting point of 169°–174°C. Analysis of Solid B showed:

| Calc. | $(C_{19}H_{24}O_5)$ | Found |
| --- | --- | --- |
| % C | 68.65 | 67.97 |
| % H | 7.28 | 7.16 |
| % OMe | 9.34 | 9.28 |

The olefinic bond of each of the dimethyl F.E.S. and monomethyl F.E.S. is reduced using 50 psi of hydrogen and a small amount of 5% Pd on charcoal catalyst in ethanol and conducting the reduction for 3 hours.

EXAMPLE XV

Monomethyl F.E.S. with the methyl group replacing the hydrogen of the hydroxyl group on the benzene ring para to the ester group was prepared by the following procedure:

Nitrosomethylurea in an amount of 1.2 grams was slowly added to a cold mixture of 3.6 milliliters of 50% potassium hydroxide and 17 milliliters of ether. After a few minutes the yellow ether layer of the mixture was decanted, dried over potassium hydroxide, and then added to a solution of 0.30 grams F.E.S. in 17 milliliters of ether. The resulting yellow mixture was left overnight in a loosely stoppered flask and then ether and diazomethane were evaporated off using a steam bath. The remaining gummy residue was crystallized by adding 3 milliliters of water, heating to 60°C., and adding ethanol almost to solution. On cooling, crystals formed, yielding 0.137 grams of a product having a melting point of 111°–116°C. which was again recrystallized in the same way to yield 0.082 grams of monomethyl F.E.S. having a melting point of 120°–122°C. and the following analysis:

| Calc. | $(C_{19}H_{24}O_5)$ | Found |
| --- | --- | --- |
| % C | 68.7 | 68.3 |
| % H | 7.28 | 7.38 |
| % $OCH_3$ | 9.34 | 9.17 |

The olefinic bond of this compound is reduced according to the procedure of Example IX.

The following example demonstrates the relatively low estrogenic activity of the compounds of the pharmaceutical compositions of the invention.

EXAMPLE XVI

A solution of each test compound identified in the table below was admixed with a standard pulverized mouse ration and the solvent was removed by evaporation to provide a dry ration containing the level of test compound per gram of feed indicated ithe table below. A control ration and each test ration were fed to 5 to 10 ovariectomized mice weighing about 20 to 23 grams each at a level of 3 grams per day for a period of 5 days after which the mice were sacrificed and their uteri weighed. An increase in the weight of the uteri from the animal fed the test compounds over the weight of the uteri in the control animals demonstrates estrogenic activity for the test compound.

The control animals showed a percent uterine weight to body weight of about 0.048 to 0.050. A uterine response of 0.060 being just significant, the dose required to give a response of 0.060 then gives the relative uterotrophic activity. The following results were obtained from curves drawn plotting dose/uterus weight as percent body weight.

| Compound | Estimated M.E.D.* | Uterotrophic Activity Relative To | |
|---|---|---|---|
| | | DES | FES |
| DES+ | 0.003 μg/g feed | 1 | 2000 |
| HMTHFES[1] | 1.25 | .0024 | 4.8 |
| LMTHFES[2] | 2.25 | .0013 | 2.7 |
| DeoxyTHFES[3] | 6.25 | .00048 | 0.96 |
| Dimethyl FES[4] | 100.0 (estimated) | .000003 | 0.06 |
| 4-methyl FES[5] | 100.0 (estimated) | .000003 | 0.06 |
| 2-methyl FES[6] | 28.0 | .000017 | 0.22 |
| Dihydro FES[7] | 3.0 | .0010 | 2.0 |
| FES | 6.0 | .0005 | 1.0 |

+diethylstilbestrol
*minimal effective dosage
[1]high melting tetra hydro FES prepared as in Example VI
[2]low melting tetra hydro FES prepared as in Example V
[3]prepared as in Example VII
[4]prepared as in Example IX
[5]prepared as in Example VIII
[6]prepared as in Example IX
[7]prepared as in Example XII

EXAMPLE XVII

Pharmaceutical preparation containing the compound of Example IV in the form of tablets suitable for administration to human patients;

246 grams of THFES(HM) is triturated with 60 grams of lactose to form an homogeneous powder. To the powder is added 20 grams of silicic acid with hydrolyzed starch and water and the mixture stirred until a homogeneous paste is formed. The paste is then dried and tabletted with 2 grams magnesium stearate to form tablets containing approximately 150 mg. of active ingredient. Similar compositions including F.E.S., THFES(LM), deoxy THFES and the alkylated and acylated compounds can be prepared by substitution of these compounds for THFES(HM) as the active ingredient.

EXAMPLE XVIII

Pharmaceutical preparation of aqueous suspension for oral administration:

Recipe for 1000 ml. of suspension

| Compound of Example III | 30.0 g. |
|---|---|
| Sucrose | 400.0 g. |
| Powdered tragacanth | 7.5 g. |
| Flavoring essential oil | 0.2 ml. |
| Methyl p-hydroxybenzoate | 2.0 g. |
| Propyl p-hydroxybenzoate | 0.5 g. |
| Glycerol | 150.0 ml. |
| Citric acid | 2.0 g. |
| Benzoic acid | 1.0 g. |
| Distilled water | (to complete 1000 ml.) |

The glycerol, benzoic acid, methyl and propyl benzoic acids, tragacanth gum, flavoring oil and active ingredient are mixed into a homogeneous mass. An aqueous solution of the citric acid is then added with slurring and finally the sucrose is added. Slurring is continued until an homogeneous suspension is obtained to which is added the balance of the water. Similar compositions including F.E.S., THFES(LM), deoxy THFES and the alkylated and acylated compounds can be prepared by substitution of these compounds for THFES(HM) as the active ingredient.

EXAMPLE XIX 100 mg. of the compound of Example III, 0.2 mg. of methyl-p-methoxybenzoate, 0.5 mg. of sodium citrate and 0.2 mg. of citric acid are added to 1 ml. of water. The pH of the suspension is adjusted to 5 with HCl. Heat sterilization results in an aqueous suspension suitable for parenteral injection.

EXAMPLES XX – XXIII

Suitable pharmaceutical compositions can be prepared by replacing the F.E.S. in the preparations of Examples XVII–XIX with any one of the compounds of Examples IV–XV.

The following examples demonstrate the cholesterol lowering effect of the active ingredients of this invention.

EXAMPLE XXIV

Male Wistar rats (Royal Hart) were allowed to eat powdered Purina Laboratory Chow ad-lib for 7 days, in order to become accustomed to eating powdered food. At a body weight of 180–200 g, the animals were then randomly assigned to groups of 8–10 animals. The animals were housed in pairs in all metal cages. Throughout the "Experimental Period" of 6 days, the animals were fed ad-lib one of the following powdered diets: (a) Plain Purina Laboratory Chow — (controls); or (b) Purina Chow containing THFES(HM). After the 6 days experimental period, the animals were exsanguinated by severing the external jugular veins under hexabarbital sodium acetate anesthesia (100 mg/kg I.P.) the blood being collected in acid-washed tubes to prevent alkaline hydrolysis of the triglycerides. The serum was separated by centrifugation, and the total cholesterol levels were estimated on the Auto-Analyzer using Standard Method No. 24a for cholesterol (Technicon Auto Analyses Procedures Manual). Body weight increases were computed from measurements of body weight at the beginning and at the end of the experimental period. Livers were dissected and weighed wet. Absolute liver weight and liver weight as a percentage of final body weight were recorded. Food consumption was monitored throughout the experimental period. The actual amount of drug ingested (in mg./kg./day) was computed from the food consumption, final body weight, and the known amount of drug in diet. Table I below shows the effects of THFES(HM) on the serum total cholesterol levels of the animals. Significant depression of serum total cholesterol was seen at doses of 6.9 mg./kg./day and above. THFES(HM) did not produce hepatomegaly under these conditions. F.E.S., THFES(LM), deoxy F.E.S. and p-methyl F.E.S. can be substituted for the THFES(HM) to treat cholesterolemia in the manner shown.

TABLE I

| Treatment | Dose* (Mg/kg/day) | Total Serum Cholesterol | | |
|---|---|---|---|---|
| | | Mean ±SEM | (mg.%) | Change as % of Control |
| Control** | | 58.8 ± | 1.7 | — |
| THFES (HM) | 1.0 | 58.5 ± | 3.3 | +1.7 |
| " | 2.1 | 57.7 ± | 2.4 | 0 |
| " | 6.9 | 49.5 ± | 2.1 | −13.8 |
| " | 8.5 | 46.6 ± | 2.6 | −19.0 |
| " | 13.2 | 41.6 ± | 1.4 | −27.6 |
| " | 16.4 | 38.1 ± | 1.7 | −34.5 |
| " | 30.0 | 33.5 ± | 2.1 | −41.4 |
| " | 53.0 | 33.5 ± | 4.4 | −41.4 |
| " | 100.0 | 24.5 ± | 1.8 | −57.0 |

*Calculated from dietary concentration of drug and food consumption.
**Mean for two experiments.

EXAMPLE XXV

Groups of 35-day old male rats (Holtzman) weighing 120–135 gm were held without treatment for 1 week on standard laboratory ration (Purina Labena Chow). The rats were then fed, ad libitum, for a 2-week period, a diet consisting of the following:

| | |
|---|---|
| Purina Labena | 50.4% |
| Cornstarch Mixture* | 29.0 |
| Lard | 20.0 |
| DL-Methionine | 0.6 |

*Cornstarch Mixture:

| | |
|---|---|
| Cornstarch | 70% |
| Alphacel | 12 |
| Crisco | 10 |
| USP Salt Mixture XIV | 7 |
| Cod Liver Oil | 1 |

During the next 2 weeks (4th and 5th on experimental diet) the animals received test compounds that were mixed in the above on a mg./kg. of diet basis. After exposure to this diet containing drug for 2 weeks the animals were anesthetized, bled individually to obtain serum samples to determine total cholesterol, triglycerides and $\alpha$- and $\beta$- lipoproteins.

The results are set forth in Table II. The chemical analysis of sera of rats on the high fat diet for 4 weeks, with drugs added for the last 2 weeks of the test period, disclosed that THFES(HM) produced highly significant decreases in total cholesterol at all doses tested and THFES(HM) decreased the $\alpha/\beta$ lipoprotein ratio to highly significant degrees at the four concentrations tested; the $\alpha/\beta$ ratios decreased with increasing concentration in the diet.

While THFES(HM) produced marked decreases in the cholesterol, triglycerides and $\alpha/\beta$- lipoprotein ratios, treatment with the compound also produced decreases in the weight gain of the animals. Based on the daily food intake values,

EXAMPLE XXVI

The effect of THFES(HM) on the vaginal and uterine mucosa and sex skin changes of ovariectomized Rhesus monkeys was determined to demonstrate the post-menapausal effects of the drug. Monkeys were studied for a period of several days prior to drug treatment to establish base-line vaginal values. THFES(HM) was administered orally for 10 days. Observations on vaginal smear changes, coloration of the sex skin and withdrawal bleeding were recorded during treatment and for 20 days following its cessation.

Administration of the drug resulted in increased numbers of cornified cells in the vaginal washings. By the 5th day of treatment with 1.8 mg/kg, leukocytes were absent from the smear and remained absent for the duration of the treatment period. Coloration of the sex skin at this dose reached its maximum on the 4th day of treatment in animal No. 13 and the 11th day in animals No. 12 and No. 14. It would appear that, at this dose level, vaginal cornification is the most sensitive indicator of the estrogenic effect of the drug. The effect on the uterus is indicated by the withdrawal bleeding which occurred in two of three animals treated; there appeared to be little uniformity in the time at which bleeding occurred following cessation of treatment.

Four of six animals treated with 0.9 mg./kg. drug had withdrawal bleeding following cessation of treatment indicating uterine stimulation; "spotting" was noted in 5 of the 6 animals. This response would suggest that 0.9 mg./kg. dose was stimulating endometrial development but was inadequate to maintain it. Vaginal changes were comparable with those observed in animals treated with the 1.8 mg./kg. dose level. Sex skin changes were present and the degree of coloration was essentially the same as was observed in the high dose group.

Animals treated with 0.45 mg./kg. drug displayed minimal or no estrogen-dependent changes. Animals No. 28, No. 29 and No. 30 showed a vaginal response

TABLE II

| Compound | Dose mg/kg Diet | No. Rats | Av. Food Intake gm/day/rat | Total Cholesterol (mg/100 ml serum) | Triglycerides | Lipo-proteins $\alpha$- | $\beta$ | $\alpha/\beta$ Ratio | Testes Wt. (gm) | Body Weight* Init. | Start | Final |
|---|---|---|---|---|---|---|---|---|---|---|---|---|
| Control | — | 10 | 13 | 98.7 ± 4.0 | 321.8 ± 46.0 | 18.3 | 27.7 | 0.66 | 3.3 | 126 | 269 | 342 |
| THFES (HM) | 12.5 | 10 | 14.7 | 72.7 ± 4.0*** | 214.2 ± 22.2* | 15.8 | 32.5 | 0.49** | 3.3 | 127 | 260 | 287 |
| THFES (HM) | 25.0 | 10 | 13.5 | 62.5 ± 3.0*** | 258.1 ± 41.1 | 11.6 | 29.7 | 0.39** | 3.2 | 128 | 264 | 278 |
| " | 50.0 | 10 | 12.4 | 59.5 ± 5.4*** | 279.2 ± 40.2 | 7.2 | 32.8 | 0.22*** | 3.1 | 127 | 255 | 255 |
| " | 100.0 | 10 | 11.0 | 52.0 ± 2.8*** | 185.4 ± 29.0 | 3.0 | 33.7 | 0.09*** | 3.1 | 128 | 260 | 246 |

*P <0.05
**P <0.01
***P <0.001
*Initial = Weight on day animals were received
 Start = Weight on day animals were placed on diet plus compound.

the estimated daily dose of THFES(HM) in these animals varied from 180 to 1100 g per rat. In addition to the findings discussed above, four of ten animals on the 12.5 mg dose level showed signs of alopecia; 1/10 of the high dose group presented this symptom. As has been indicated in other studies there was involution of the thymus in treated animals. F.E.S. and deoxy THFES can be substituted for the THFES(HM) to treat hypercholesterolemia in a similar manner.

The following examples demonstrate that the active ingredient of this invention is effective in estrogenic replacement therapy in post-menapausal and similar treatments.

which persisted throughout the study. Animal No. 2' had "spotting" as judged by the presence of RBC's i its smear on 11 treatment or post-treatment days. An mals No. 23, No. 24 and No. 26 treated at a differer time, failed to respond.

Based upon the data, it can be concluded tha THFES(HM) is able to stimulate estrogen-like change in ovariectomized monkeys and can be used as a pos! menapausal drug.

EXAMPLES XXVII–XXX

In each of these examples, 10 women were adminis tered THFES(HM) at varying dosage levels for a p( riod of time. Tables III to VI set forth the relevant data for post-menapausal response. The administration of the drug and dosage was

| TABLE | DOSAGE | TEST PERIOD |
|---|---|---|
| Table III | 400 mg./daily | 20 days |
| Table IV | 200 mg./daily | 20 days |
| Table V | 100 mg./daily | 60 days |
| Table VI | 50 mg./daily | 30 days |

The prior symptoms appear with the patient identification and the effect of the drug is shown under Remarks. The data demonstrate the effectiveness of THFES(HM) in relieving many of the symptoms at the dosage levels tested. At 200 mg./daily the symptoms, with the exception of insomnia, were relieved. At 100 mg./daily the symptoms were relieved and the patients showed excellent estrogenic response with the exception of Patient 63-A. There were no toxic symptoms evident. With an average weight per patient of about 50 kg., the dosages levels are about 1 to 8 mg./day/kg. body weight. The follicle stimulating hormones (FSH) data of Table V are a clear demonstration of the activity of the drug in treatment of post-menopausal syndrome since to lower the FSH units in a good measure of such activity.

TABLE III

| Patient | Age | Day | Vaginal Cytology Basal Cells | CPI | EI | Leucocytes | Remarks |
|---|---|---|---|---|---|---|---|
| 39-A Had vulvular pruritis and insomnia. Diabetes mellitus in good control with diet. Biopsy - resting endom. | 62 | 0 7 14 21 21 Biopsy - Late prolif. endometrium. Moderate mitotic activity. | 77% 0 0 0 | 23 38 56 | 64 61 87 | Many Some v.few None | Shortly after start - patient feeling well with slight decrease of vulvar itching and wetness of vulva and vagina. Did not have withdrawal bleeding. Discontinued - lack of drug. |
| 40-A Suffers hot flushes and irritability. Biopsy - Early prolif, endom. Scarce mitotic activity. | 51 | 0 7 14 20 20 Biopsy - Late prolif endometrium. Patchy hyperplasia. | 17 0 | 6 32 45 67 | 19 56 39 48 | Some Some v.few v.few | Complete disappearance of hot flushes. Improvement of psychological state. Discontinued - lack of drug. Withdrawal bleeding lasted 3 days. |
| 41-A Periodic diarrhea and dryness of genitalia. Irritability of colon since age 30. Biopsy- Resting endometrium. | 59 | 0 7 14 20 20 Biopsy - Late prolif. endometrium. Good mitotic activity. | 34 6 | 2 21 59 48 | 10 36 83 71 | | Colon condition unchanged. Genitalia moist. Has had normal intercourse with husband. Scant withdrawal bleeding lasting 2 days. Discontinued - lack of drug. |
| 42-A Depression, irritability and mild hot flushes. Biopsy - Intermed. prolif. endom. Scarce mitotic activity. | 52 | 0 7 14 20 20 Biopsy - Late prolif. endometrium. Good mitotic activity. | 11 | 19 24 52 63 | 6 51 60 57 | Some Few Few Few | Hot flushes and irritability disappeared. Still depressed. No withdrawal bleeding. Discontinued - lack of drug. |
| 43-A Obese; has insomnia and frequent headaches. Biopsy - atrophic endom. with areas of cystic pseudo-hyperplasia. | 59 | 0 7 14 20 20 Biopsy - Late prolif. endom. with moderate mitotic activity. | 31 2 | 7 32 51 59 | 22 26 64 47 | | No headaches. Insomnia did not improve. Slight withdrawal bleeding that lasted 2 days. Discontinued - lack of drug. |
| 44-A Hot flushes and dysparennia. Cholecistectomy in 1961. Biopsy - Intermed. prolif. endom. Scarce mitotic activity. | 51 | 0 7 14 20 20 Biopsy - Late prolif. endometrium. Good mitotic activity. | 24 0 | 12 38 67 77 | 3 63 100 91 | | Hot flushes disappeared. Dyspareunia minimal. No withdrawal bleeding. Discontinued - lack of drug. |
| 45-A Marked dryness of genitalia - discrete burning sensation. Has moderate hypertension. Biopsy - atrophic endometrium. | 63 | 0 7 14 20 20 Biopsy - Late prolif. endometrium. Moderate mitotic activity. | 87 marked inflammatory exudate 14 0 | 38 63 68 | 22 71 90 | - Several Some | Markedly relieved - epithelia of the genitalia are moist - burning sensation disappeared. No withdrawal blending. Discontinued - lack of drug. |
| 46-A Easy fatigability and irritability. Biopsy - resting endometrium. | 56 | 0 7 14 20 20 Biopsy - Late prolif. endometrium. Patchy hyperplasia. | 18 | 13 39 68 73 | 22 63 70 69 | Several Some Some Few | Marked decrease of irritability; still gets tired easily; Withdrawal bleeding lasted 4 days and was moderate. Discontinued - lack of drug. |

TABLE III-continued

| Patient | Age | Day | Vaginal Cytology Basal Cells | CPI | EI | Leuco-cytes | Remarks |
|---|---|---|---|---|---|---|---|
| 47-A<br>No gynecological complaints - chronic colitis.<br>Biopsy - Inactive endometrium | 59 | 0<br>7<br>14<br>20<br>20 Biopsy - Late prolif. endom. Moderate mitotic activity. | 43 | 11<br>43<br>51<br>73 | 2<br>90<br>67<br>82 | Some<br>Few<br>Few<br>No | No ill effects - had slight mucorrhea lasting 2 days. Withdrawal bleeding moderate lasting 2 days. Discontinued - lack of drug. |
| 48-A<br>Abdominal discomfort rare; marked hot flushes and moderate depression.<br>Biopsy -<br>Late prolif. endom.<br>Slight mitotic activity. | 52 | 0<br>7<br>14<br>20<br>20 Biopsy - Late prolif. endometrium. Good mitotic activity. | | 23<br>53<br>87<br>79 | 30<br>68<br>82<br>94 | Some<br>v.few<br>v.few<br>v.few | Abdominal discomfort and hot flushes disappeared. Remains depressed. No withdrawal bleeding. Discontinued - lack of drug. |

TABLE IV

| Patient | Age | Day | Vaginal Cytology Basal Cells | CPI | EI | Leuco-cytes | Remarks |
|---|---|---|---|---|---|---|---|
| 49-A<br>Discrete depression and fainting spells.<br>Biopsy - Inactive endometrium. | 55 | 0<br>7<br>14<br>20<br>20 Biopsy - intermed. prolif. endom. - Moderate mitotic activity. | | 8<br>28<br>24<br>31 | 2<br>19<br>36<br>22 | Few<br>Few<br>Few<br>Few | Feels same as before starting drug. No withdrawal bleeding. Discontinued - lack of drug. |
| 50-A<br>Minor complaints on GF tract; bouts of diarrhea. Emotionally unstable.<br>Biopsy - atrophic endometrium. | 60 | 0<br>7<br>14<br>20<br>20 Biopsy - intermed. prolif. endom. Moderate mitotic activity. | 61<br>32 | 21<br>53<br>47 | 7<br>67<br>83 | Several<br><br>Some<br>Some | Condition remained the same during treatment, although genitalia became wet. Discontinued - lack of drug. |
| 51-A<br>Slight itching and leukorrhea; irritability for past 20 years.<br>Biopsy - none. | 65 | 0<br>7<br>14<br>20<br>20 Biopsy - Late prolif. endom. Moderate mitotic activity. | 68 | 2<br>63<br>56<br>59 | 7<br>70<br>82<br>67 | Many<br>Some<br>Few<br>Few | Itching and Leukorrhea disappeared. Psychological state did not change. Minimal withdrawal bleeding for one day. Discontinued - lack of drug. |
| 52-A<br>Suffers dyspareunia, headaches, insomnia.<br>Biopsy - intermed. prolif. endometrium - few mitoses. | 54 | 0<br>7<br>14<br>20<br>20 Biopsy - Late prolif. endometrium. Moderate mitotic activity. | 4 | 23<br>38<br>30<br>47 | 32<br>40<br>31<br>38 | Some<br>Few<br>Some<br>Few | Increased wetness of vagina and decrease of dyspareunia. Headache and insomnia not affected. No withdrawal bleeding. Discontinued - lack of drug. |
| 53-A<br>Dryness of vulva and vagina - slight burning sensation worse at night<br>Biopsy - atrophic endometrium | 65 | 0<br>7<br>14<br>20<br>20 Biopsy - Late prolif. endometrium. Slight mitotic activity. | 86 | 32<br>67<br>73 | 53<br>84<br>69 | Many<br>Many<br>Some<br>Some | Complete disappearance of complaints. Regrets no more drug available. No withdrawal bleeding. Discontinued - lack of drug. |
| 54-A<br>Marked irritability - infrequent but very hot flushes<br>Biopsy - atrophic endom. - cystic pseudohyperplasia. | 53 | 0<br>7<br>14<br>20<br>20 Biopsy - Late prolif. endometrium. Moderate mitotic activity. | 22<br>6 | 12<br>22<br>48<br>36 | 4<br>19<br>36<br>49 | Some<br>Some<br>Some<br>Some | No hot flushes during treatment. First days of treatment moderate nausea. One episode of epigastric burning. Irritability did not change. No withdrawal bleeding. Discontinued - lack of drug. |
| 55-A<br>Hot flushes and palpitations.<br>Biopsy - Intermed. prolif. endom.<br>Scarce mitotic activity | 50 | 0<br>7<br>14<br>20<br>20 Biopsy - Late prolif. endometrium. Slight hyperplasia. | | 15<br>42<br>59<br>53 | 23<br>38<br>64<br>71 | Several<br>Few<br>Few<br>Few | No hot flushes; palpitations unchanged. Epigastric burning first few days. Moderate withdrawal bleeding lasted 3 days. Discontinued - lack of drug. |

TABLE IV-continued

| Patient | Age | Day | Vaginal Cytology Basal Cells | CPI | EI | Leucocytes | Remarks |
|---|---|---|---|---|---|---|---|
| 56-A Dryness of vulva and marked dyspareunia last 2 years. Biopsy - resting endometrium. | 58 | 0 7 14 20 20 Biopsy - Late prolif. endometrium. Moderate mitotic activity. | 73 22 | 19 38 71 | 24 57 64 | Many Several Some Few | Marked improvement with disappearance of dyspareunia. No withdrawal bleeding. Discontinued - lack of drug. |
| 57-A Extremely irritable with frequent hot flushes Biopsy - Intermed. prolif. endom. Very few mitoses. | 53 | 0 7 14 20 20 Biopsy - Late prolif. endometrium. Good mitotic activity. | | 10 48 36 57 | 0 30 63 75 | Few Few Few Few | Hot flushes gone and feels much better. Regrets no more drug. Withdrawal bleeding moderate - lasted two days. Discontinued - lack of drug. |
| 58-A Palpitation, moderate respiratory insufficiency, easy fatigability. Widow. Biopsy - none | 64 | 0 7 14 20 20 Biopsy - Late prolif. endometrium. Slight mitotic activity. | 74% 16 | 3 28 31 57 | 0 12 42 49 | Many Several Several Some | Patient remained in same state. No withdrawal bleeding. Discontinued - lack of drug. |

TABLE V

| Patient | Age | Day | Vaginal Cytology Basal Cells | CPI | EI | Leucocytes | Follicle Stimulating Hormone | Remarks |
|---|---|---|---|---|---|---|---|---|
| 59-A Hot blushes; nausea in the morning. Biopsy - resting endometrium. | 52 | 0 10 20 30 30 Biopsy - Prolif. endom. Moderate mitotic activity. | 64% 11 | 6 27 63 50 | 47 54 62 | Several Some Some Some | 0d. 52 m.u. 45d. 6 m.u. | Under treatment 50 days, after 10 days symptoms disappeared. No problems. |
| 60-A Asthenia and numbness of hands. Menopause 4 years ago. Biopsy - Early prolif. endom. Scarce mitotic activity | 50 | 0 10 20 30 30 Biopsy - Late prolif. endometrium. Moderate mitotic activity. | | 7 35 59 68 | 16 49 37 49 | Several Several Several Some | 0d. 112 m.u. 60d. 12 m.u. | Under treatment 54 days. Marked improvement 10 to 15 days after start. No problems. |
| 61-A Hot flushes and slight irritability. Biopsy - Resting endometrium. | 49 | 0 10 20 30 30 Biopsy - Late prolif. endometrium. Slight mitotic activity. | | 5 27 63 58 | 0 55 42 60 | Many Several Several | | Symptoms disappeared after 2 weeks. No problems. |
| 62-A Asthenia and irritability. Biopsy - None. | 51 | 0 10 20 30 30 Biopsy - Late prolif. endometrium. Moderate mitotic activity. | 87% 2 | 3 19 63 51 | 24 40 66 | Many Some Some Some | 0d. 64 m.u. 30d. 6 m.u. 60d. >6 m.u. | Symptoms improved 6 or 7 days after start. Asthenia gone after 15 days. Irritability markedly decreased. No problems. |
| 63-A Hot flushes and itching of genitalia. Biopsy - resting endometrium. | 57 | 0 10 20 30 30 Biopsy - Intermed. prolif. endometrium. Slight mitotic activity. | 93% 22 | 0 30 36 42 | 12 43 35 | Many Several Several Several | 0d. 120 m.u. 30d. 10 m.u. | Hot flushes disappeared after 7 to 10 days. Itching decreased but did not vanish. After 2 weeks tenderness of breasts and bloating. She interrupted treatment. |
| 64-A Hot blushes and sporadic diarrhea. Biopsy - Early prolif. endom. Minimal mitotic activity. | 55 | 0 10 20 30 30 Biopsy - Late prolif. endometrium. Good mitotic activity. | | 9 35 45 56 | 16 55 38 50 | Several Several Several Several | 0d. 97 m.u. 30d. 9 m.u. 60d. 6 m.u. | Hot blushes gone in less than 7 days. Three of diarrhea. No other problem. |
| 65-A Hot blushes and insomnia. Biopsy - resting endometrium. | 63 | 0 10 20 30 30 Biopsy - Intermed. endom. Moderate mitotic activity. | 78% 32 3 | 4 16 32 29 | 10 38 62 | Several Several Some Some | 0d. 185 m.u. 30d. <6 m.u. 60d. <6 m.u. | Hot blushes disappeared and insomnia improved. Feeling very well. |

TABLE V-continued

| Patient | Age | Day | Basal Cells | CPI | EI | Leuco-cytes | Follicle Stimulating Hormone | Remarks |
|---|---|---|---|---|---|---|---|---|
| 66-A<br>Moderate irritability and headaches, also mild diabetes mellitus.<br>Biopsy - None. | 64 | 0<br>10<br>20<br>30 | 86%<br>33<br><br>6 | 0<br>30<br>33<br>45 | <br>17<br>46<br>32 | Many<br>Many<br>Several<br>Several | 0d. 97 m.u.<br>60d. 12 m.u. | Decrease in number of headaches and intensity. Mild nausea first days. Vomited once. |
|  |  | 30 Biopsy - Late prolif. endometrium. Slight mitotic activity. | | | | | | |
| 67-A<br>Hot blushes, nervousness, sporadic headaches. Menopause - 2 years ago. Biopsy - Late prolif. endom. Scarce mitotic activity. | 49 | 0<br>10<br>20<br>30 | 0 | 10<br>28<br>62<br>58 | 2<br>45<br>57<br>83 | Some<br>Some<br>Few<br>Few | 0d. 106 m.u.<br>7d. 31 m.u.<br>14d. 25 m.u.<br>21d. 13 m.u.<br>28d. 6 m.u.<br>60d. <6 m.u. | Hot blushes and headaches disappeared shortly after start. Nervousness improved but not gone. |
|  |  | 30 Biopsy - Late prolif. endometrium. Patchy hyperplasia. | | | | | | |
| 68-A<br>Complete hysterectomy and ovariectomy. Had severe hot blushes and irritability. Biopsy-not done (hysterectomy) | 34 | 0<br>10<br>20<br>30 | 98%<br>13<br>6 | <br>37<br>50<br>67 | <br>52<br>43<br>80 | Several<br>Some<br>Some<br>Few | 0d. 168 m.u.<br>30d. 14 m.u.<br>60d. <6 m.u. | Feeling well. Symptoms gone after 1.0 week. |
|  |  | 30 Biopsy - None | | | | | | |

TABLE VI

| Patient | Age | Day | Basal Cells | CPI | EI | Leuco-cytes | Remarks |
|---|---|---|---|---|---|---|---|
| 79-A<br>Hot blushes and nervousness.<br>Biopsy - atrophic endometrium. Cystic pseudohyperplasia. | 52 | 0<br>10<br>20<br>30 | 42%<br>23 | 6<br>14<br>26<br>46 | <br>28<br>20<br>35 | Several<br>Several<br>Several<br>Several | Hot blushes gone after 3 weeks. Remains very nervous. |
|  |  | 30 Biopsy - Intermed. prolif. endom. Moderate mitotic activity. | | | | | |
| 80-A<br>Diarrhea (chronic amoebiasis). Depressed.<br>Biopsy - resting endometrium. | 64 | 0<br>10<br>20<br>30 | 93%<br>37<br>30<br>0 | <br>11<br>28<br>37 | <br><br><br>28 | Many<br>Several<br>Several<br>Several | Patient feels same and reports no change. |
|  |  | 30 Biopsy - Early prolif. endometrium. Moderate mitotic activity. | | | | | |
| 81-A<br>Marked irritability frequent hot flushes, some severe headaches.<br>Biopsy - resting endometrium. | 50 | 0<br>10<br>20<br>30 | 0 | 11<br>35<br>63<br>57 | 31<br>30<br>48<br>62 | Several<br>Several<br>Some<br>Some | Hot blushes gone after 15-20 days. No headaches and moderate decrease in irritability. |
|  |  | 30 Biopsy - Late prolif. endometrium. Good mitotic activity. | | | | | |
| 82-A<br>Irritability, mild hot blushes and insomnia - past 2 years. Diabetic.<br>Biopsy - resting endometrium | 56 | 0<br>10<br>20<br>30 | 69%<br>31<br>8 | 0<br>27<br>19<br>38 | <br><br><br>51 | Many<br>Several<br>Several<br>Some | Patient has not improved. |
|  |  | 30 Biopsy - Late prolif. endometrium. Patchy hyperplasia. | | | | | |
| 83-A<br>Atrophic vaginitis. Hysterectomy in 1953 Marked varicose veins.<br>Biopsy - hysterectomy | 69 | 0<br>10<br>20<br>30 | 100%<br>71<br>17<br>4 | 0<br>20<br>48<br>37 | | Many<br>Many<br>Several<br>Several | Good condition. Vaginal inflammation improved. |
|  |  | 30 Biopsy - None | | | | | |
| 84-A<br>Periods of mild depression or irritability.<br>Biopsy - Early prolif. endom. Scarce mitotic activity. | 56 | 0<br>10<br>20<br>30 | | 18<br>36<br>31<br>40 | 7<br>38<br>54<br>36 | Several<br>Some<br>Few<br>Few | Condition same as before start of treatment. |
|  |  | 30 Biopsy - Late prolif. endometrium. Moderate mitotic activity. | | | | | |
| 85-A<br>Intense, frequent hot blushes. Occasional nausea and mild headaches.<br>Biopsy - Not enough material. | 52 | 0<br>10<br>20<br>30 | 21% | 13<br>39<br>36<br>42 | 6<br>16<br>44<br>29 | Several<br>Some<br>Some<br>Some | Slight improvement of all symptoms 10-15 days after start of drug. |
|  |  | 30 Biopsy - Late prolif. endometrium. Patchy hyperplasia. | | | | | |

TABLE VI-continued

| Patient | Age | Day | Basal Cells | Vaginal Cytology CPI | EI | Leucocytes | Remarks |
|---|---|---|---|---|---|---|---|
| 86-A | 53 | 0 | | 12 | 3 | Several | Hot blushes disappeared. In- |
| Insomnia, moderate | | 10 | | 36 | 51 | Some | somnia and nervousness un- |
| depression, mild | | 20 | | 27 | 50 | Some | changed. |
| occasional hot | | 30 | | 47 | 26 | Some | |
| blushes. Biopsy - | | 30 Biopsy - Late prolif. | | | | | |
| Early prolif. endom. | | endometrium. Moderate | | | | | |
| Scarce mitotic activity. | | mitotic activity. | | | | | |
| 87-A | 66 | 0 | 96% | 0 | | Many | Vaginitis improved but has not |
| Kraurosis vulvae, | | 10 | 70 | 16 | | Many | disappeared. |
| atrophic vaginitis | | 20 | | 35 | 52 | Many | |
| with moderate | | 30 | | 28 | 27 | Many | |
| leukorrhea. | | 3 Biopsy - Intermed. | | | | | |
| Biopsy - mocoid | | prolif. endom. Slight | | | | | |
| material. | | mitotic activity. | | | | | |
| 88-A | 49 | 0 | | 11 | 21 | Some | Hot blushes gone 3 weeks after |
| Marked frequent hot | | 10 | | 30 | 55 | Few | start. Nervousness the same. |
| blushes and moderate | | 20 | | 33 | 38 | Few | |
| nervousness. | | 30 | | 28 | 47 | Few | |
| Biopsy - Early prolif. | | 30 Biopsy - Late prolif. | | | | | |
| endom. Slight mitotic | | endometrium. Poor | | | | | |
| activity | | mitotic activity. | | | | | |

The terms "hot blushes" and "hot flushes" are used synonymously herein.

EXAMPLES XXXI and XXXII

Tables VI and VII below set forth the results of tests in which two groups of 10 women were fed, respectively, 200 mg./day and 100 mg./day of F.E.S. In the test summarized in Table VI the drug was administered daily for 60 days whereas in the test summarized in Table VII the drug was administered in a regime of 25 days on the drug followed by a 10 day rest period over a total time period of 180 days. Treatment at 100 mg./daily relieved most of the post-menapausal symptoms with the exception of insomnia and depression. Treatment at 200 mg./daily did not relieve insomnia.

TABLE VII

| Patient | Age | Day | Basal Cells | Vaginal Cytology CPI | EI | Leucocytes | Remarks |
|---|---|---|---|---|---|---|---|
| 139-A | 61 | 0 | 99% | 0 | 0 | Many | Disappearance of symptoms re- |
| Suffers mild, well- | | 10 | 62 | 20 | 7 | Many | lated to genitalia. Head- |
| controlled diabetes. | | 20 | 31 | 27 | 19 | Several | aches unaffected. No |
| Has headache and dry- | | 30 | 7 | 30 | 19 | Several | withdrawal bleeding. |
| ness with itching of | | 60 Late prolif. endom. | | | | | |
| external genitalia. | | Good mitotic activity. | | | | | |
| 140-A | 39 | 0 | | 100 | 0 | 0 | Many | Patient well. No mor hot |
| Had ovariohysterec- | | 10 | | 52 | 26 | 13 | Some | blushes and feels very re- |
| tomy 8-67. Early | | 20 | | 21 | 38 | 54 | Some | laxed. No withdrawal |
| in October had hot | | 30 | | 3 | 42 | 80 | Few | bleeding. |
| blushes and nervousness. | | | | | | | |
| 141-A | | Early prolif. endom. | | | | | |
| | | Scarce mitotic activity. | | | | | |
| | 56 | 0 | | 3 | 11 | Several | Feels better but still has in- |
| Suffers insomnia and | | 10 | | 26 | 31 | Several | somnia. After second course |
| slight depression. | | 20 | | 38 | 63 | Some | had few drops of withdrawal |
| | | 30 | | 46 | 45 | Some | bleeding. |
| | | Late prolif. endom. | | | | | |
| | | Moderate mitotic activity. | | | | | |
| 142-A | | Resting endom. | | | | | |
| | 56 | 0 | 26 | 4 | 0 | Several | No hot blushes since treatment |
| Marked nervousness | | 10 | 13 | 16 | 36 | Some | started. Nervousness im- |
| and occasional hot | | 20 | 2 | 37 | 29 | Some | proved moderately. |
| blushes. | | 30 | 0 | 46 | 38 | Some | |
| | | Intermed. prolif. endom. | | | | | |
| | | Discrete mitotic activity. | | | | | |
| 143-A | 57 | | Atrophic endom. with | | | | |
| | | | pseudohyperplasia. | | | | |
| | | 0 | 17 | 2 | 9 | Few | No change. No withdrawal |
| Mild nervousness. | | 10 | | 26 | 33 | Few | bleeding. |
| | | 20 | | 29 | 57 | Few | |
| | | 30 | | 40 | 58 | Few | |
| | | 30 | Intermed. prolif. endom. | | | | |
| | | | Moderate mitotic activity. | | | | |
| 144-A | 69 | | No biopsy. | | | | |
| Suffered pyelonephritis | | 0 | 100 | 0 | 0 | Several | Patient has mild renal insuffi- |
| and has atrophy and | | 10 | 64 | 10 | 7 | Several | ency. Genitalia wetter with |
| dryness of vulva. | | 20 | 30 | 29 | 18 | Several | occasional slight mucorrhea. |
| | | 30 | 7 | 35 | 52 | Several | No withdrawal bleeding. |
| | | 60 | Early prolif. endom. | | | | |
| | | | Slight mitotic activity. | | | | |

TABLE VII-continued

| Patient | Age | Day | Vaginal Cytology Basal Cells | CPI | EI | Leuco-cytes | Remarks |
|---|---|---|---|---|---|---|---|
| 145-A<br>Last menstrual period (LMP) 5/14. Has frequent hot blushes and feels nervous. On drug 11/14 | 49 | 0<br>10<br>20<br>30<br>60 | Early prolif. endom.<br>Discrete mitotic activity.<br><br><br><br>Late prolif. endom.<br>Patchy hyperplasia. | 13<br>35<br>48<br>66 | 26<br>30<br>39<br>50 | Some<br>Some<br>Few<br>Few | No more hot blushes after one week on drug. After end of second course had vaginal bleeding which was discrete. |
| 146-A<br>Moderate nervousness and bouts of diarrhea | 54 | 0<br>10<br>20<br>30 | Early prolif. endom.<br>Slight mitotic activity<br>14 | 6<br>21<br>38<br>35 | 23<br>29<br>34<br>62 | Several<br>Some<br>Some<br>Some | Feels better but has had two episodes of diarrhea. After second course had moderate withdrawal bleeding for two days. |
| 147-A<br>LMP 13 mo. prior to drug. Has frequent hot blushes and marked irritability. | 51 | 0<br>10<br>20<br>30<br>60 | Resting endometrium.<br>66<br>9<br>7<br>1<br>Intermed. prolif. endom.<br>Slight mitotic activity. | 3<br>21<br>39<br>46 | 0<br>38<br>32<br>52 | Several<br>Some<br>Some<br>Some | Hot blushes disappeared shortly after started drug and irritability improved slightly. No withdrawal bleeding. |
| 148-A<br>Has mild diabetes and atrophic vulvular vaginitis. | 65 | 0<br><br>10<br>20<br>30 | No biopsy.<br>100<br>54<br>20<br>13 | 0<br>3<br>35<br>56 | 0<br>17<br>23<br>60 | Many + oandida albicans<br>Many<br>Several<br>Several | Besides drug patient received anti-monilial drugs. Vulvovaginitis cured. No withdrawal bleeding. |

TABLE VIII

| Patient | Age | Day | Vaginal Cytology Basal Cells | CPI | EI | Leuco-cytes | Remarks |
|---|---|---|---|---|---|---|---|
| 119-A<br>Has hypertension and intense vulvar itching. Has diabetes mellitus controlled by dieting. No endometrial biopsy before treatment. | 62 | 0<br>10<br>20<br>30 | 79%<br>36<br>17<br>6<br>Endometrial biopsy after 20 days - Intermediate prolif. endometrium. Slight activity. | 0<br>7<br>30<br>37 | 2<br>10<br>21<br>47 | Many<br>Several<br>Several<br>Some | Itching improved after one week and disappeared after 3 weeks. No withdrawal bleeding but some mucorrhea. Schedule: 25 days on drug - 10 days off. 180 day Biopsy - Late Proliferative endometrium. Good mitotic activity. At 180 days - Patient feeling well. Slight withdrawal bleeding for 3 days after four months of treatment. |
| 120-A<br>Infrequent hot blushes and moderate nervousness. Biopsy - intermed. prolif. endom. with slight mitotic activity. | 53 | 0<br>10<br>20<br>30 | 9<br><br><br><br>20 day Biopsy - Late prolif. endom. with moderate mitotic activity. | 10<br>23<br>51<br>40 | 3<br>36<br>67<br>58 | Some<br>Some<br>Few<br>Few | Marked improvement after 5 to 10 days of treatment. She has been feeling well. Moderate withdrawal bleeding after second course of treatment. Schedule: 25 days on drug - 10 days off. At 180 days - Biopsy - Late proliferative endometrium with good mitotic activity. Feeling well. From third to sixth cycle no withdrawal bleeding. |
| 121-A<br>Has frequent headaches and insomnia. Biopsy - atrophic endom. with cystic pseudohyperplasia. | 58 | 0<br>10<br>20<br>30 | 14<br>3<br><br><br>60 day Biopsy - prolif. endom. with patchy hyperplasia. | 3<br>26<br>38<br>31 | 13<br>17<br>62<br>70 | Several<br>Some<br>Few<br>Few | Headache improved but not insomnia. Few drops of blood after third course. Schedule: 25 days on drug - 10 days off. Biopsy - 180 days - Proliferative endometrium with patchy hyperplasia. 180 days - Slight withdrawal bleeding on fourth and sixth cycles. Feeling well. |
| 122-A<br>Moderate irritability and depression. Biopsy - inactive endometrium. | 61 | 0<br>10<br>20<br>30 | 64<br>24<br>18<br>3<br>30 day Biopsy - prolif. endom. Slight mitotic activity. | 1<br>27<br>18<br>40 | 13<br>42<br>58<br>37 | Many<br>Few<br>Few<br>Few | Feeling a little better. No withdrawal bleeding. Schedule: 25 days on drug - 10 days off. 180 days biopsy - Late proliferative endometrium. Feels depressed - no withdrawal bleeding. |

TABLE VIII-continued

| Patient | Age | Day | Basal Cells | Vaginal Cytology CPI | EI | Leuco- cytes | Remarks |
|---|---|---|---|---|---|---|---|
| 123-A<br>Frequent intense hot blushes with abdominal pain and flatulence. Biopsy - early prolif. endom. with poor mitotic activity. | 50 | 0<br>10<br>20<br>30<br>60 day biopsy - Late prolif. endom. with good mitotic activity. | | 16<br>46<br>35<br>58 | 24<br>37<br>58<br>65 | Some<br>Some<br>Few<br>Few | After one week of treatment, hot blushes decreased in number and intensity and disappeared after 20 days. Flatulence has decreased but not disappeared. Schedule: 25 days on drug - 10 days off. 180 day biopsy - Late Proliferative endometrium with moderate mitotic activity. Patient has episodes of abdominal discomfort, otherwise feels well. No withdrawal bleeding. |
| 124-A<br>Kraurosis vulvae and moderate itching. Biopsy - resting endometrium. | 68 | 0<br>10<br>20<br>30<br>30 day biopsy - Early prolif. endom. with slight mitotic activity. | 98<br>80<br>53<br>21 | 0<br>0<br>11<br>35 | 0<br>7<br>28<br>31 | Many<br>Many<br>Several<br>Several | Itching improved; vulvar mucosa slightly wet. No withdrawal bleeding. Schedule: 25 days on drug - 10 days off. 180 day biopsy - Intermediate proliferative endometrium with poor mitotic activity. Feeling well. No withdrawal bleeding. |
| 125 A<br>Moderately frequent hot blushes; rare headaches Biopsy - atrophic endom. with cystic pseudo- hyperplasia. | 52 | 0<br>10<br>20<br>30<br>30 day biopsy - prolif. endom. with moderate mitotic activity. | | 8<br>51<br>35<br>60 | 3<br>34<br>62<br>48 | Some<br>Some<br>Some<br>Some | No headaches and hot blushes disappeared after one week on drug. Minimal withdrawal bleeding after third course. Schedule: 25 days on drug - 10 days off. 180 day biopsy - Late proliferative endometrium with patchy hyperplasia. Occasional headaches fifth month and slight withdrawal bleeding on fifth month. |
| 126-A<br>Irritability and periods of depression. Biopsy - resting endometrium. | 58 | 0<br>10<br>20<br>30<br>30 day biopsy - Early prolif. endom. Moderate mitotic activity. | 47<br>37<br>26<br>8 | 1<br>8<br>17<br>31 | 13<br>20<br>19<br>43 | Many<br>Several<br>Several<br>Several | Irritability improved but still depressed over family problems. No withdrawal bleeding. Schedule: 25 days on drug - 10 days off. 180 day biopsy - Late proliferative endometrium with discrete mitotic activity. Depressed. Has forgotten to take several capsules. No withdrawal bleeding. |
| 127-A<br>Slight nervousness and hypertension. Biopsy - resting endometrium. | 55 | 0<br>10<br>20<br>30<br>60 day biopsy - late proliferative endometrium. Moderate mitotic activity. | 37<br>20<br>7<br>11 | 8<br>17<br>35<br>47 | 3<br>29<br>23<br>61 | Several<br>Some<br>Some<br>Few | Remained without significant change; likely nervousness decreased. No withdrawal bleeding. Schedule: 25 days on drug - 10 days off. 180 day biopsy - Early proliferative endometrium with moderate mitotic activity. Irritability improved. No withdrawal bleeding. |
| 128-A<br>Marked and frequent hot blushes with frequent moderate headaches. Biopsy - early prolif. endom. with moderate mitotic activity. | 49 | 0<br>10<br>20<br>30<br>30 day biopsy - late prolif. endometrium. Good mitotic activity. | | 14<br>23<br>28<br>55 | 26<br>31<br>63<br>42 | Many<br>Many<br>Several<br>Several | Symptoms improved in five days and disappeared after 15 days. Feeling well. Moderate withdrawal bleeding after second and third courses. Schedule: 25 days on drug - 10 days off. 180 day biopsy - Proliferative endometrium with patchy hyperplasia. Feeling well. Moderate withdrawal bleeding in fifth and sixth months. |

EXAMPLE XXXIII

Groups I, II, III and IV each composed of human female patients suffering postmenapausal syndrome were orally given dosages of 10, 25, 50 and 100 mgs./day, respectively, of pure Compound II (LM) having a melting point of about 155°C. for 3 cycles, each cycle consisting of taking the compound daily for 20 days followed by a 10 day period during which the patient abstains from taking the compound. The results are set forth below.

The pure Compound II (LM) can be separated from a mixture of it and its high melting diastereoisomer by solubilizing the mixture in glacial acetic acid and crystallizing out the pure Compound II (LM) in accordance with the process described in the copending patent application of Vernon V. Young, Ser. No. 643,819, filed June 6, 1967, now Pat. No. 3,574,235, herein incorporated by reference.

| GROUP | DOSE[1] | FSH (units)[2] | | VAGINAL CYTOLOGY[3] CPI | | SUBJECTIVE RESPONSE[4] |
|---|---|---|---|---|---|---|
| | | INITIAL | 90 DAYS TREATMENT | INITIAL | 20-DAYS | 90 Days |
| I | 10 mg. | 105(144–66) | 25.8(54–6) | 5.2(18–0) | 24.7(38–16) | 4 of 10 |
| II | 25 mg. | 102(156–66) | 22.2(36–6) | 7.6(19–0) | 40.8(52–26) | 8 of 10 |
| III | 50 mg. | 92.8(138–54) | 12.0(30–6) | 5.5(11–0) | 55.2(73–42) | 10 of 10 |
| IV | 100 mg. | 99(150–60) | 11.4(30–6) | 11.0(19–0) | 67.5(77–59) | 9 of 10 |

[1]Dose mg. orally daily for 20 days with a 10 day rest.
[2]Follicle stimulating hormone assay before and after 3 cycles of treatment.
[3]Chorionic pycnotic index.
[4]Subjective response as reported to physician by patient.

It is claimed:

1. A method of treating post-menapausal syndrome in a human female having such syndrome which comprises internally administering to said human an amount sufficient to relieve said syndrome of a compound of the formula selected from the group consisting of:

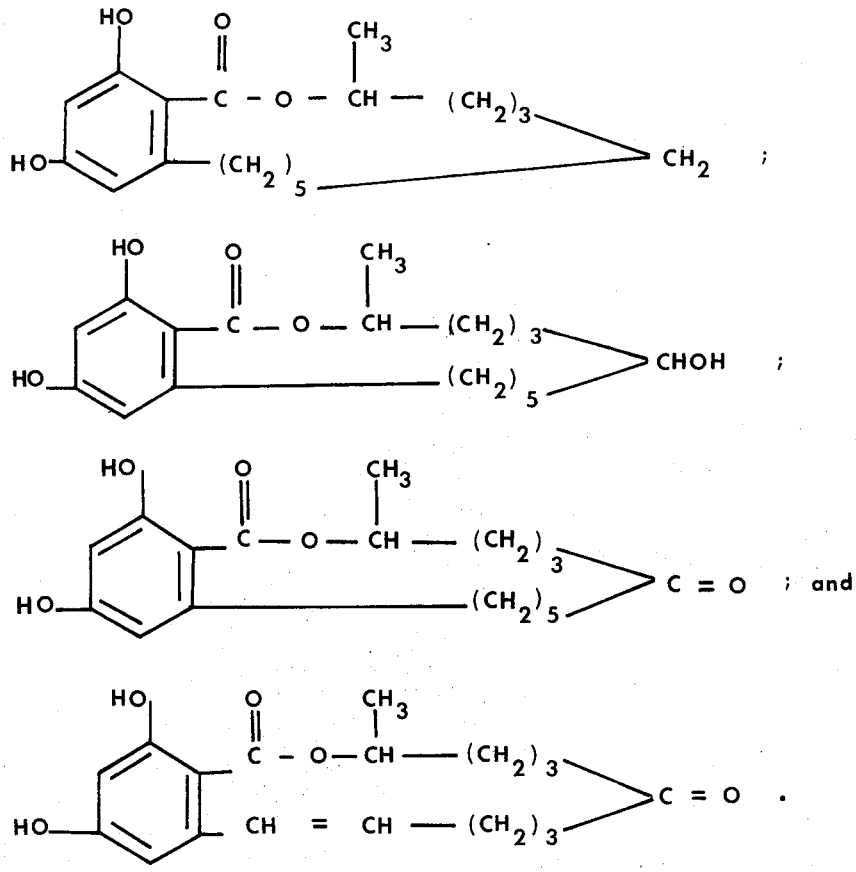

2. The method of claim 1 wherein the compound is orally administered.

3. The method of claim 2 wherein the compound is administered in a cycle of 20 to 25 days of administration followed by a rest period of 5 to 10 days.

4. The method of claim 3 wherein the compound is administered to said human in an amount of about 0.1 to 10 mg. per day per kilogram body weight of said human.

5. The method of claim 4 wherein said compound is the diastereoisomer of the formula

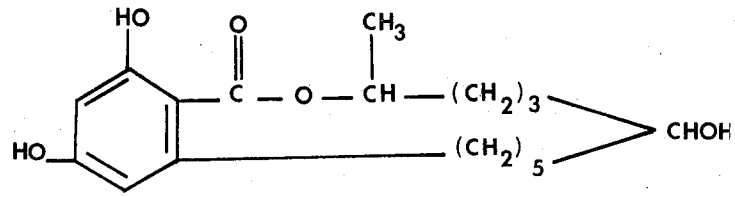

having a melting point of about 155°C.
6. The method of claim 1 wherein said compound is the diastereoisomer of the formula
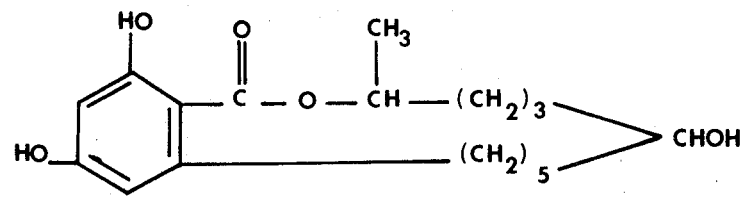
having a melting point of about 178°–180°C.
* * * * *